United States Patent
Kauffman et al.

(10) Patent No.: US 6,492,107 B1
(45) Date of Patent: *Dec. 10, 2002

(54) PROCESS FOR OBTAINING DNA, RNA, PEPTIDES, POLYPEPTIDES, OR PROTEIN, BY RECOMBINANT DNA TECHNIQUE

(75) Inventors: Stuart Alan Kauffman, Sante Fe, NM (US); Marc Ballivet, Geneva (CH)

(73) Assignee: Stuart Kauffman, Santa Fe, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/464,569

(22) Filed: Jun. 5, 1995

Related U.S. Application Data

(63) Continuation of application No. 08/349,510, filed on Dec. 2, 1994, now Pat. No. 5,723,323, which is a continuation of application No. 08/133,952, filed on Oct. 8, 1993, now abandoned, which is a continuation of application No. 07/977,307, filed on Nov. 16, 1992, now abandoned, which is a continuation of application No. 07/616,319, filed on Nov. 21, 1990, now abandoned, which is a continuation of application No. 06/942,630, filed on Nov. 20, 1986, now abandoned.

(51) Int. Cl.$^7$ .......................... C12Q 1/68; G01N 33/53; C07H 21/04; C07K 14/00
(52) U.S. Cl. .......................... 435/6; 435/7.1; 435/69.1; 435/91.1; 435/194; 435/243; 435/320.1; 435/455; 435/471; 530/300; 530/350; 536/23.1
(58) Field of Search .................... 435/6, 91.2, 7.1–7.9, 435/69.1, 91.1, 194, 243, 320.1, 455, 471; 536/24.3–24.33, 23.1; 530/300, 350

(56) References Cited

U.S. PATENT DOCUMENTS

| | | | | |
|---|---|---|---|---|
| 4,366,246 A | * | 12/1982 | Riggs ........................... | 435/68 |
| 4,366,264 A | | 12/1982 | Riggs | |
| 4,490,358 A | | 12/1984 | Greene et al. | |
| 4,634,678 A | * | 1/1987 | Salstrom et al. | |
| 4,959,312 A | * | 9/1990 | Sirotkin ........................ | 435/91 |

FOREIGN PATENT DOCUMENTS

| | | |
|---|---|---|
| DE | 3303173 | 2/1984 |
| DE | 3246071 | 6/1984 |
| DE | 3300632 | 12/1984 |

OTHER PUBLICATIONS

Maniatis et al 1982 In Molec. Cloning; A Lab Manual; CSH Press; pp. 217–228.*
Botstein et al 1985 Science 229:1193–1201.*
Childs et al 1985 du Sequence Specificity in Transcription and Translation; Liss Publisher pp. 341–350.*
Fox et al 1968 Science 160:547–548.*
Ohno. 1984 (Apr.) Proc Natl Acad. Sci 81:2421–2425.*
Milkman et al 1983 Science 221:378–380.*
Holmquist 1979 Science 203:1012–1014.*
Fox 1969 Die Naturwissenschafter 56:1–9.*
Ibanez et al 1971 Science 173:444–446.*
Hoffmann 1975 Annual Review of Phys. Chem. 26:123–144.*
Carter et al., "Improved Oligonucleotides Site–directed Mutagenesis using M13 Vectors," *Nucleic Acids Res.* 4431–4443 (1985).
Craik C., "Use of Oligonucleotides for Site–Specific Mutagenesis, " *Biotechniques* 3:12 (1985).
Efimov et al., "Effective method of oligonucleotide–controlled mutagenesis of DNA fragments," *Bioorg. Khim.* 621–627, May 1985.
Gearing et al., "Chemical synthesis of a mitochondrial gene designed for expression in the yeast nucleous," *Biochem. Int.* 907–915 (1985).
Hoffman, "The stochastic theory of the origin of the genetic code," *Annu. Review Of Physical Chemistry* 26:123–144 (1975).
Zoller and Smith, "Oligonucleotide–Directed Mutagenesis: A Simple Method using Two Oligonucleotides Primers and a Single–Stranded DNA Template," *Mutagenesis and Protein Engineering.*
Belfort et al., "Genetic System for Analyzing *Escherichia coli* Thymidylate Synthase," *J. Bact.* 160:371–378 (1984).
Biebricher and Orgel, "An RNA That Multiplies Indefinitely With DNA–Dependent RNA Polymerase: Selection from a Random Copolymer," *Proc. Natl. Acad. Sci. USA* 70(3):934–938 1973.
Borrias et al., "Induction and isolation of mutants in a specific region of gene A of bacteriophage ΦX 174," *Virology* 70(1):195–197 (1976).
Busby S., "Isolation of mutant promoters in the *Escherichia coli* galactose operon using local mutagenesis on cloned DNA fragments," *J. Mol. Biol.* 154(2):197–209 (1982).
Carter et al., "Improved Oligonucleotide Site–directed Mutagenesis using M13 Vectors," *Nucleic Acids Res.* 4431–4443 (1985)★.*

(List continued on next page.)

*Primary Examiner*—Stephanie Zitomer
(74) *Attorney, Agent, or Firm*—Campbell & Flores LLP

(57) ABSTRACT

The present invention is directed to a process for the production of a peptide, polypeptide, or protein having a predetermined property. In accordance with one embodiment, the process begins by producing by way of synthetic polynucleotide coupling, stochastically generated polynucleotide sequences. A library of expression vectors containing such stochastically generated polynucleotide sequences is formed. Next, host cells containing the vectors are cultured so as to produce peptides, polypeptides, or proteins encoded by the stochastically generated polynucleotide sequences. Screening or selection is carried out on such host cells to identify a peptide, polypeptide, or protein produced by the host cells which has the predetermined property. The stochastically generated polynucleotide sequence which encodes the identified peptide, polypeptide, or protein is then isolated and used to produce the peptide, polypeptide, or protein having the predetermined property.

12 Claims, No Drawings

OTHER PUBLICATIONS

Chu et al., "Hydroxylamine mutagenesis of HSV DNA and DNA fragments: indtroduction of mutations into selected regions of the viral genome," *Virology* 98(1): 168–181 (1979).*

Clune et al., "Affinity engineering of maltoporin: variants with enhanced affinity for particular ligands," *Biochem–Biophys. Res. Commun.* 121(1):34–40 (1984).*

Craik C., "Use of Oligonucleotides for Site–Specific Mutagenesis," *Biotechniques* 3:12 (1985)★.*

Damiani et al., "Sequence analysis of heteropolymeric DNA synthesized in vitro by the enzyme terminal deoxynucleotidyl transferase and cloned in *Escherichia coli*," *Nucleic Acids Res.* 10(20):6401–6410 (1982).*

DiMaio and Nathans, "Cold–sensative regulatory mutants of simian virus 40," *J. Mol. Biol.* 140(1) 129–142 (1980).*

DiMaio and Nathans, "Regulatory mutants of simian virus 40. Effect of mutations at a T antigen binding site on DNA replication and expression of viral genes," *J. Mol. Biol.* 156(3) 531–548 (1982).*

Efimov et al., "Convenient modification of the method for oligonucleotide–directed in vitro mutagenesis of cloned DNA," *FEBS Lett.* 181(2):407–411, (1985).*

Efimov et al., "Effective method of oligonucleotide–controlled mutagenesis of DNA fragments," *Bioorg. Khim.* 621–627, May 1985★.*

Engebrecht and Silverman, "Identification of genes and gene products necessary for bacterial bioluminescence," *Proc. Natl. Acad. Sci. USA* 81:4154–4158 (1984).*

Estell et al., "Engineering an enzyme by site–directed mutagenesis to be resistant to chemical oxidation," *J. Biol. Chem.* 260(11):6518–6521 (1985).

Fasano et al., "Analysis of the transforming potential of the human H–ras gene by random mutagenesis," *Proc. Natl. Acad. Sci. USA* 81:4008–4012 (1984).

Gearing et al., "Chemical synthesis of a mitochondrial gene designed for expression in the yeast nucleous," *Biochem. Int.* 907–915 (1985)★.

Haltiner et al., "A novel strategy for constructing clustered point mutations," *Nucleic Acids Res.* 13(3):1015–1025 (1985).

Hirose et al., "In vitro characterization of the fibroin gene promoter by the use of single–base substitution mutants," *Proc. Natl. Acad. Sci. USA* 79(23) 7258–7562 (1982).

Hoffman, "The stochastic theory of the origin of the genetic code," *Annu. Review of Physical Chemistry* 26:123–144 (1975)★.

Itakura et al., "Synthesis and use of synthetic oligonucleotides," *Annu. Rev. Biochem.* 53:323–356 (1984).

Kadonaga and Knowles, "A Simple and Efficient Method for Chemical Mutagenesis of DNA," *Nucleic Acids Res.* 13(5):1733–1745 (1985).

Kalderon et al., "Deletion loop mutagenesis: a novel method for the construction of point mutations using deletion mutants," *Nucleic Acids Res.* 10(17):5161–71 (1982).

Kalderon and Smith, "In Vitro Mutagenesis of a putative DNA Binding Domain of SV40 Large–T," *Virology* 139:109–137 (1984).

Kunkel T., "Rapid and Efficient Site–Specific Mutagenesis without Phenotypic Selection," *Proc. Natl. Acad. Sci. USA* 82:488–492 (1985).

Morona et al., "*Escherichia coli* K–12 outer membrane protein (OmpA) as a bacteriophage receptor: analysis of mutant genes expressing altered proteins," *J. Bacteriol.* 159:570–578 (1984).*

Muller et al., "Site–Directed Mutagenesis in DNA: Genereation of Point Mutations in Cloned β Globin Complementary DNA at the Positions Corresponding to Amino Acids 121 to 123," *J. Mol. Biol.* 124:343–358 (1978).*

Myers et al., "Modification of the Melting Properties of Duplex DNA by Attachment of a GC–rich DNA Sequence as Determined by Denaturing Gradient Gel Electrophoresis," *Nucleic Acids Res.* 13(9):3111–3129 (1985).*

Myers et al., "Nearly all Single Base Substitutions in DNA Fragments Joined to a GC–clamp Can Be Detected by Denaturing Gradient Gel Electrophoresis," *Nucleic Acids Res.* 13(9): 3131–3145 (1985).*

O'Connor and Stohrer, "Site–specifically modified oligodeoxyribonucleotides as Templates for *Escherichia coli* DNA polymerase I," *Proc. Natl. Acad. Sci. USA* 82:2325–2329 (1985).*

Oostra et al., "Transforming activity of polyoma virus middle–T antigen probed by site–directed mutagenesis," *Nature* 304:456–459 (1983).*

Peden and Nathans, "Local Mutagenesis within deletion Loops of DNA Heteroduplexes," *Proc. Natl. Acad. Sci. USA* 79:7214–7217 (1982).*

Shortle and Nathans, "Local Mutagenesis: A Method for Generating Viral Mutants with Base Substitutions in Preselected Regions of the Viral Genome," *Proc. Natl. Acad.Sci. USA* 75(5):2170–2174 (1978).*

Shortle and Botstein, "Directed Mutagenesis with Sodium Bisulfite," *Methods–Enzymol.* 100:457–468 (1983).*

Shortle and Lin, "Genetic Analysis of Staphylococcal Nuclease: Identification of Three Intragenic "Global" Suppressors of Nuclease–Minus Mutations," *Genetics* 110:539–555 (1985).

Shortle et al., "Directed Mutagenesis," *Annu. Rev. Genet.* 15:265–294 (1981).

Solnick D., "An Adernovirus Mutant Defective in Splicing RNA from Early Region 1A," *Nature* 291:508–511 (1981).

Stone et al., "Identification of Functional Regions in the Transforming Protein of Fujinami Sarcoma Virus by In–Phase Insertion Mutagenesis," *Cell* 37:549–558 (1984).

Vos et al., "Study of the genetic organisation of a plant viral RNA genome by in vitro expression of a full–length DNA copy," *EMBO Journal* 3(13): 3049–3053 (1984).

Warburton et al., "Increased expression of a cloned gene by local mutagenesis of its promoter and ribosome binding site," *Nucleic Acids Res.* 11(17):5837–5854 (1983).

Waye et al., "EcoK Selection Vectors for Shotgun Cloning in to M13 and Deletion Mutagenesis," *Nucleic Acids Res.* 13(23):8561–8571 (1985).

Youderian et al., "Changing the DNA–Binding Specificity of a Repressor," *Cell* 35:777–783 (1983).

Zakour et al., "Site specific mutagenesis: insertion of single noncomplementary nucleotides at specified sites by error–directed DNA polymerization," *Nucleic Acids Res.* 12(16):6615–6628 (1984).

Zarucki et al., "Point Mutagenesis of the Ovalbumin Gene Promoter Sequence and Its Effect on In Vitro Transcription," *J. Biol. Chem.* 257(18):11070–11077 (1982).

Zoller and Smith, "Oligonucleotide–Directed Mutagenesis of DNA Fragments Cloned in to M13 Vectors," *Methods in Enzymology* 100:468–500 (1983).

Zoller and Smith, "Oligonucleotide–Directed Mutagenesis: A Simple Method using Two Oligonucleotides Primers and a Single–Stranded DNA Template," *Mutagenesis and Protein Engineering*★.

Childs et al., In Sequence Specificity in Transcription and Translation, pp. 341–350, Alan Liss, 1985.*

Shirm et al., EMBO J. 4: 2669–74, 1985.*

Kreuzer et al., JMB 188: 185–198, 1986.*

Kalderon et al. Nature 311:33–36, 1984.*

Stinchcomb et al. PNAS 77: 4559–4563, 1980.*

Oka et al. Gene 19: 59–70, 1982.*

Ruby et al. Methods Enzymol 101:253–69, 1989.*

Weber et al. EMBO j. 4: 949–56, 1985.*

Geyson et al, PNAS 3998–4002, 1984.*

Houghton, PNAS 82: 5131–5135, 1985.*

Ellington and Szostak, Nature 346:818–822, 1990.*

Tuerk and Gold, Science 249: 505–510, 1990.*

Cwiria et al. PNAS 87:6378–6382, 1990.*

Beardsley, "New Order: Artificial evolution creates proteins nature missed," *Scientific American* 263:18 (1990).

Botstein and Shortle, "Strategies and Applications of in Vitro Mutagenesis, " *Science* 229:1193 (1985).

Buell et al., "Optimizing the expression in *E. coli* of a synthetic gene encoding somatomedin–C IGF–I," *Nucleic Acids Research* 13:1923 (1985).

Charney et al., "Linker Scanning Mutagenesis of the 5'–Flanking Region of the Mouse β–Major–Globin Gene: Sequence Requirements for Transcription in Erythroid and Nonerythroid Cells," *Molecular and Cellular Biology* 5:1498 (1985).

Geysen et al., "Use of peptide synthesis to probe viral antigens for epitopes to a resolution of a single amino acid," *Proc. Natl. Acad. Sci.* 81:3998 (1984).

Grundström et al., "Oligonucleotide–directed mutagenesis by microscale 'shot–gun' gene synthesis," *Nucleic Acids Research* 13:3305 (1985).

Hermes et al., *Proc. Natl. Acad. Sci.* 87:696 (1990).

Hill et al., "Mutagenesis with degenerate oligonucleotides," (1987).

Horwitz et al., "Selection of new biological activities from random nucleotide sequence". (1989).

Hoffman, G.W., *Chemical Abstracts* 84(5):136, Abstract No. 26960x (1976).

Houghten, "General method for the rapid solid–phase synthesis of large numbers of peptides: Specificity of antigen–antibody interaction at the level of individual amino acids," *Proc. Natl. Acad. Sci.*, 82:5131 (1985).

Hui et al., "Mutagenesis of the three bases preceding the start codon of the β–galactosidase mRNA and its effect on translation in *Escherichia coli*," *The EMBO Journal* 3(3):623–629 (1984).

Kalderon et al., "Sequence requirements for nuclear location of simian virus 49 large–T antigen," *Nature* 311:33–36 (1984).

Lewin, "The universal construction set," *New Scientist* 30 (1990).

Ma and Ptashne, *Cell* 51:113 (1987).

Maniatis et al. *Molec. Cloning: A Lab Manual*, CSH Press, pp. 217–228 (1982).

Matteucci and Heyneker, "Targeted random mutagenesis: the use of ambiguously synthesized oligonuccleotides to synthesize sequences immediately 5' of an ATG initation codon," *Nucleic Acids Research* 11:3113 (1983).

McNeil and Smith, "*Saccharomyces cerevisiae* CYCI mRNA 5–end Positioning: Analysis by In Vitro Mutagenesis, Using Synthetic Duplexes with Random Mismatch Base Pairs," *Molecular and Cellular Biology* 5:3545 (1985).

Milkman et al., *Science* 221:378–380 (1983).

Murphy and Baralle, "Directed semisynthetic point mutational analysis of an RNA polymerase III promoter," *Nucleic Acids Research* 11:7895 (1983).

Myers et al., "A General Method for Saturation Mutagenesis of Cloned DNA Fragments," *Science* 229:242 (1985).

Ohno, *Proc. Natl. Acad. Sci.* 81:2421–2425 (1984).

Oliphant et al., *Gene* 44:177 (1986).

Scott and Smith, "Searching for Peptide Ligands with an Epitope Library," *Science* 249:386 (1990).

Shortle et al., "Gap misrepair mutagenesis: Efficient site–directed induction of transition, transversion, and frameshift mutations in vitro,"*Proc. Natl. Acad. Sci.*, 79:1588 (1982).

Smith, "In Vitro Mutagenesis," *Ann. Rev. Genet.*, 19:423 (1985).

Taylor et al., "The rapid generation of oligonucleotide–directed mutations at high frequency using phosphorothioate–modified DNA," *Nucleic Acids Research* 13:8765 (1985).

Traboni et al., "A general method to select for M13 clones carrying base pair substitution mutants constructed in vitro," *Nucleic Acids Research*, 11:4229 (1983).

Tuerk and Gold, "Systematic Evolution of Ligands by Exponential Enrichment: RNA Ligands to Bacteriophage T4 DNA Polymerase," *Science* 249:505 (1990).

Wells et al., "Cassette mutagenesis: an efficient method for generation of multiple mutations at defined sites," *Gene* 34:315 (1985).

Zakour and Loeb, "Site–specific mutagenesis by error–directed DNA synthesis," *Nature* 295:708 (1982).

Childs et al., "Ribosome Binding Site Sequences and Function," *Sequence Specificity in Transcripton and Translation*, Alan R. Liss, Inc., pp. 341–350 (1985).*

Cwirla et al., "Peptides on Phage: A Vast Library of Peptides for Identifying Ligands". *Proc. Natl. Acad. Sci. USA* 87:6378–6382 (1990).*

Devlin et al., "Random Peptide Libraries: A Source of Specific Protein Binding Molecules". *Science* 249:404–406 (1990).*

Dube et al., "Mutants generated by insertion of random oligos into active site of the β–lactamase gene".*

Eisenbeis et al., "Altered Cro repressors from engineered mutagnesis of a synthetic cro gene," *Proc. Natl. Acad. Sci.* 82:1084 (1985).*

Efstratiadis et al., "Cloning of Double–Stranded cDNA," *Genetic Engineering, Principals and Methods* 1:15–36, Plenum Press (1979).*

Ellington and Szostak, *Nature* 346:818 (1990).*

Fox et al., *Science* 160:547–548 (1968).*

* cited by examiner

PROCESS FOR OBTAINING DNA, RNA, PEPTIDES, POLYPEPTIDES, OR PROTEIN, BY RECOMBINANT DNA TECHNIQUE

CROSS REFERENCE TO RELATED APPLICATION

This application is a continuation of application Ser. No. 08/349,510, filed Dec. 2, 1994, now U.S. Pat. No. 5,723,323, which is a continuation of application Ser. No. 08/133,952, filed Oct. 8, 1993, now abandoned, which is a continuation of application Ser. No. 07/977,307, filed Nov. 16, 1992, now abandoned, which is a continuation of application Ser. No. 07/616,319, filed Nov. 21, 1990, now abandoned, which is a continuation of application Ser. No. 06/942,630, filed Nov. 20, 1986, now abandoned, the entire disclosures all of which are incorporated herein by reference.

This invention was made with government grant support under GM 22341 awarded by the United States Office of Naval Research. The United States government has certain rights in the invention.

Priority of Switzerland patent application serial no. 1379/85-8, filed Mar. 30, 1985, is claimed through PCT International Application No. PCT/CH85/00099, filed Jun. 17, 1985, under 35 U.S.C. §§120/365.

The present invention has as its object a process for obtaining DNA, RNA, peptides, polypeptides, or proteins, through use of transformed host cells containing genes capable of expressing these RNAs, peptides, polypeptides, or proteins; that is to say, by utilization of recombinant DNA technique.

The invention aims in particular at the production of stochastic genes or fragments of stochastic genes in a fashion to permit obtaining simultaneously, after transcription and translation of these genes, a very large number (on the order of at least 10,000) of completely new proteins, in the presence of host cells (bacterial or eukaryotic) containing these genes respectively capable of expressing these proteins, and to carry out thereafter a selection or screen among the said clones, in order to determine which of them produce proteins with desired properties, for example, structural, enzymatic, catalytic, antigenic, pharmacologic, or properties of liganding, and more generally, chemical, biochemical, biological, etc. properties.

The invention also has as its aim procedures to obtain, sequences of DNA or RNA with utilizable-properties notably chemical, biochemical, or biological properties.

It is clear, therefore, that the invention is open to a very large number of applications in very many areas of science, industry, and medicine.

The process for production of peptides or polypeptides according to the invention is characterized in that one produces simultaneously, in the same medium, genes which are at least partially composed of synthetic stochastic polynucleotides, that one introduces the genes thus obtained into host cells, that one cultivates simultaneously the independent clones of the transformed host cells containing these genes in such a manner so as to clone the stochastic genes and to obtain the production of the proteins expressed by each of these stochastic genes, that one carries out selection and/or screening of the clones of transformed host cells in a manner to identify those clones producing peptides or polypeptides having at least one desired activity, that one thereafter isolates the clones thus identified and that one cultivates them to produce at least one peptide or polypeptide having the said property.

In a first mode of carrying out this process, stochastic genes are produced by stochastic copolymerization of the four kinds of deoxyphosphonucleotides, A, C, G and T from the two ends of an initially linearized expression vector, followed by formation of cohesive ends in such a fashion as to form a stochastic first strand of DNA constituted by a molecule of expression vector possessing two stochastic sequences whose 3' ends are complementary, followed by the synthesis of the second strand of the stochastic DNA.

In a second mode of carrying out this process, stochastic genes are produced by copolymerization of oligonucleotides without cohesive ends, in a manner to form fragments of stochastic DNA, followed by ligation of these fragments to a previously linearized expression vector.

The expression vector can be a plasmid, notably a bacterial plasmid. Excellent results have been obtained using the plasmid pUC8 as the expression vector.

The expression vector can also be viral DNA or a hybrid of plasmid and viral DNA.

The host cells can be prokaryotic cells such as HB 101 and C 600, or eukaryotic cells.

When utilizing the procedure according to the second mode mentioned above, it is possible to utilize oligonucleotides which for a group of palindromic octamers. Particularly good results are obtained by utilizing the following group of palindromic octamers:

5' GGAAT7CC 3'
5' GGTCGACC 3'
5' CAAGCTTG 3'
5' CCATATGG 3'
5' CATCGATG 3'

It is also possible to use oligonucleotides which form a group of palindromic heptamers.

Very good results are obtained utilizing the following group of palindromic heptamers:

5' XTCGCGA 3'
5' XCTGCAG 3'
5' RGGTACC 3' where X=A, G, C, or T, and R=A or T

According to a method to utilize these procedures which is particularly advantageous, one isolates and purifies the transforming DNA of the plasmids from a culture of independent clones of the transformed host cells obtained by following the procedures above, then the purified DNA is cut by at least one restriction enzyme corresponding to specific enzymatic cutting site present in the palindromic octamers or heptamers but absent from the expression vector which was utilized; this cutting is followed by inactivation of the restriction enzyme, then one simultaneously treats the ensemble of linearized stochastic DNA fragments thus obtained with T4 DNA ligase, in such a manner to create a new ensemble of DNA containing new stochastic sequences, this new ensemble can therefore contain a number of stochastic genes larger than the number of genes in the initial ensemble. One then utilizes this new ensemble of transforming DNA to transform the host cells and clone these genes, and finally utilizes screening and/or selection and isolates the new clones of transformed host cells and finally these are cultivated to produce at least one peptide or polypeptide, for example, a new protein.

The property serving as the criterion for selection of the clones of host cells can be the capacity of the peptides or polypeptides, produced by a given clone, to catalyze a given chemical reaction.

For instance, for the production of several peptides and/or polypeptides, the said property can be the capacity to catalyze a sequence of reactions leading from an initial group of chemical compounds to at least one target compound.

With the aim of producing an ensemble constituted by a plurality of peptides and polypeptides which are reflexively autocatalytic, the said property can be the capacity to catalyze the synthesis of the same ensemble from amino acids and/or oligopeptides in an appropriate milieu.

The said property can also be the capacity to modify selectively the biological or chemical properties of a given compound, for example, the capacity to selectively modify the catalytic activity of a polypeptide.

The said property can also be the capacity to stimulate, inhibit, or modify at least one biological function of at least one biologically active compound, chosen, for example, among the hormones, neurotransmitters, adhesion factors, growth factors, and specific regulators of DNA replication and/or transcription and/or translation of RNA.

The said property can equally be the capacity of the peptide or polypeptide to bind to a given ligand.

The invention also has as its object the use of the peptide or polypeptide obtained by the process specified above, for the detection and/or the titration of a liquid.

According to a particularly advantageous mode of carrying out the invention, the criterion for selection of the clones of transformed host cells is the capacity of these peptides or polypeptides to simulate or modify the effects of a biologically active molecule, for example, a protein, and screening and/or selection for clones of transformed host cells producing at least one peptide or polypeptide having this property, is carried out by preparing antibodies against the active molecule, then utilizing these antibodies after their purification, to identify the clones containing this peptide or polypeptide, then by cultivating the clones thus identified, separating and purifying the peptide or polypeptide produced by these clones, and finally by submitting the peptide or polypeptide to an in vitro assay to verify that it has the capacity to simulate or modify the effects of the said molecule.

According to another mode of carrying out the process according to the invention, the property serving as the criterion of selection is that of having at least one epitope similar to one of the epitopes of a given antigen.

The invention carries over to obtaining polypeptides by the process specified above and utilizable as chemotherapeutically active substances.

In particular, in the case where the said antigen is EGF, the invention permits obtaining polypeptides usable for chemotherapeutic treatment of epitheliomas.

According to a variant of the procedure, one identifies and isolates the clones of transformed host cells producing peptides or polypeptides having the property desired, by affinity chromatography against antibodies corresponding to a protein expressed by the natural part of the DNA hybrid.

For example, in the case where the natural part of the hybrid DNA contains a gene expressing β-galactosidase, one can advantageously identify and isolates the said clones of transformed host cells by affinity chromatography against anti-β-galactosidase antibodies. After expression and purification of hybrid peptides or polypeptides, one can separate and isolate their novel parts.

The invention also applies to a use of the process specified above for the preparation of a vaccine; the application is characterized by the fact that antibodies against the pathogenic agent are isolated, for example, antibodies formed after injection of the pathogenic agent in the body of an animal capable of forming antibodies against this agent, and these antibodies are used to identify the clones producing at least one protein having at least one epitope similar to one of the epitopes of the pathogenic agent, the transformed host cell corresponding to these clones are cultured to produce these proteins, this protein is isolated and purified from the clones of cells, then this protein is used for the production of a vaccine against the pathogenic agent.

For example in order to prepare an anti-HVB vaccine, one can extract and purify at least one capsid protein of the HVB virus, inject this protein into an animal capable of forming antibodies against this protein having at least one epitope similar to one of the epitopes of the HVB virus, then cultivate the clones of transformed host cells corresponding to these clones in a manner to produce this protein, isolate and purify the protein from culture of these clones of cells and utilize the protein for the production of an anti-HVB vaccine.

According to an advantageous mode of carrying out the process according to the invention, the host cells consist in bacteria such as *Escherichia coli* whose genome contains neither the natural gene expressing β-galactosidase, nor the EBG gene, that is to say, $Z^-$, EBG-*E. coli*. The transformed cells are cultured in the presence of X gal and the indicator 1PTG in the medium, and cells positive for β-galactosidase functions are detected; thereafter, the transforming DNA is transplanted into an appropriate clone of host cells for large scale culture to produce at least one peptide or polypeptide. The property serving as the criterion for selection of the transformed host cells can also be the capacity of the polypeptides or proteins produced by the culture of these clones to bind to a given compound.

This compound can be in particular chosen advantageously among peptides, polypeptides, and proteins, notably among proteins regulating the transcription activity of DNA.

On the other hand, the said compound can also be chosen among DNA and RNA sequences.

The invention has also as its object those proteins which are obtained in the case where the property serving as criterion of selection of the clones of transformed host cells consist in the capacity of these proteins to bind to regulatory proteins controlling transcription activity of the DNA, or else to DNA and RNA sequences.

The invention has, in addition, as an object, the use of a protein which is obtained in the first particular case above mentioned, as a cis-regulatory sequence controlling replication or transcription of a neighboring DNA sequence.

On the other hand, the aim of the invention also includes utilization of proteins obtained in the second case mentioned to modify the properties of transcription or replication of a sequence of DNA, in a cell containing the sequence of DNA, and expressing this protein.

The invention has as its object as well as a process of production of DNA, characterized by simultaneous production in the same medium, of genes at least partially composed of stochastic synthetic polynucleotides, in that the genes thus obtained are introduced into host cells to produce an ensemble of transformed host cells, in that screening and/or selection on this ensemble is carried out to identify those host cells containing in their genome stochastic sequences of DNA having at least one desired property, and finally, in that the DNA from the clones of host cells thus identified is isolated.

The invention further has as its object a procedure to produce RNA, characterized by simultaneous production in the same medium, of genes at least partially composed of stochastic synthetic polynucleotides, in that the genes thus obtained are introduced into host cells to produce an ensemble of transformed host cells, in that the host cells so produced are cultivated simultaneously, and screening and/or selection of this ensemble is carried out in a manner to identify those host cells containing stochastic sequences of RNA having at least one desired property, and in that the RNA is isolated from the host cells thus identified. The said property can be the capacity to bind a given compound, which might be, for example, a peptide or polypeptide or protein, or also the capacity to catalyze a given chemical reaction, or the capacity to be a transfer RNA.

Now the process according to the invention will be described in more details, as well as some of its applications, with reference to non-limitative embodiments.

First we shall describe particularly useful procedures to carry out the synthesis of stochastic genes, and the introduction of those genes in bacteria to produce clones of transformed bacteria.

I) Direct Synthesis on an Expression Vector
a) Linearization of the Vector 30 micrograms, that is, approximately $10^{13}$ molecules of the pUC8 expression vector are linearized by incubation for 2 hours at 37° C. with 100 units of the Pst1 restriction enzyme in a volume of 300 μl of the appropriate standard buffer. The linearized vector is treated with phenol-chloroform then precipitated in ethanol, taken up in volume of 30 μl and loaded onto a 0.8% agarose gel in standard TEB buffer. After migration in a field of 3V/cm for three hours, the linearized vector is electro-eluted, precipitated in ethanol, and taken up in 30 μl of water.

b) Stochastic Synthesis using the Enzyme Terminal Transferase (TdT)

30 ug of the linearized vector are reacted for 2 hours at 37° C. with 30 units of TdT in 300 μl of the appropriate buffer, in the presence of 1 mM dGTP, 1 mM dCTP, 0.3 mM dTTP and 1 mM DATP. The lower concentration of dTTP is chosen in order to reduce the frequence of "stop" codons in the corresponding messenger RNA. A similar result, although somewhat less favorable, can be obtained by utilizing a lower concentration for dATP than for the other deoxynucleotide triphosphates. The progress of the polymerization on the 3' extremity of the Pst1 sites is followed by analysis on a gel of aliquots taken during the course of the reaction.

When the reaction attains or passes a mean value of 300 nucleotides added per 3' extremity, it is stopped and the free nucleotides are separated from the polymer by differential precipitation or by passage over a column containing a molecular sieve such as Biogel P60. After concentration by precipitation in ethanol, the polymers are subjected to a further polymerization with TdT, first in the presence of dATP, then in the presence of dTTP. These last two reactions are separated by a filtration on a gel and are carried out for short intervals (30 seconds to 3 minutes) in order to add sequentially 10–30 A followed by 10–30 T to the 3' ends of the polymers.

c) Synthesis of the Second Strand of Stochastic DNA

Each molecule of vector possess, at the end of the preceding operation, two stochastic sequences whose 3' ends are complementary. The mixture of polymers is therefore incubated in conditions favoring hybridization of the complementary extremities (150 mM NaCl, 10 mM Tris-HCl, pH 7.6, 1 mM EDTA at 65° for 10 minutes, followed by lowering the temperature to 22° C. at a rate of 3 to 4° C. per hour). The hybridized polymers are then reacted with 60 units of the large fragment (Klenow) of polymerase 1, in the presence of the four nucleotide triphosphates (200 mM) at 4° C. for two hours. This step accomplishes the synthesis of the second strand from the 3' ends of the hybrid polymers. The molecules which result from this direct synthesis starting from linearized vector are thereafter utilized transform competent cells.

d) Transformation of Competent Clones 100 to 200 ml of competent HB 101 of C 600 at a concentration of $10^{10}$ cells/ml, are incubated with the stochastic DNA preparation (from above) in the presence of 6 mM CaCl$_2$, 6 mM Tris-HCl pHG, 6 mM MgCl$_2$ for 30 minutes at 0° C. A temperature shock of 3 minutes at 37° C. is imposed on the mixture, followed by the addition of 400 to 800 ml of NZY culture medium, without antibiotics. The transformed culture is incubated at 37° C. for 60 minutes, then diluted to 10 litres by addition of NZY medium containing 40 μg/ml of ampicillin. After 3–5 hours of incubation at 37° C., the amplified culture is centrifuged, and the pellet of transformed cells is lyophilysed and stored at −70° C. Such a culture contains $3 \times 10^7$ to $10^8$ independent transformants, each containing a unique stochastic gene inserted into the expression vector.

II) Synthetic of Stochastic Genes Starting from Oligonucleotides without Cohesive Ends This procedure is based on the fact that polymerization of judiciously chosen palindromic oligonucleotides permits construction of stochastic genes which have no "stop" codon in any of the six possible reading frames, while at the same time assuring a balanced representation of triplets specifying all amino acids. Further, and to avoid a repetition of sequence motifs in the proteins which result, the oligonucleotides can contain a number of bases which is not la multiple of three. The example which follows describes the use of one of the possible combinations which fulfill these criteria:

a) Choice of a Group of Octamers

The group of oligonucleotides following:

5' GGAATTCC 3'

5' GGTCGACC 3'

5' CAAGCTTG 3'

5' CCATATGG 3'

5' CATCGATG 3' is composed of 5 palindromes (thus self-complementary sequences) where it is easy to verify that their stochastic polymerization does not generate any "stop" codons, and specifies all the amino acids.

Obviously, one can utilize other groups of palindromic octamers which do not generate any "stop" codons and specify all the amino acids found in polypeptides. Clearly, it is also possible to utilize non-palindromic groups of octamers, or other oligomers, under the condition that their complements forming double stranded DNA are also used.

b) Assembly of a Stochastic Gene from a Group of Octamers

A mixture containing 5 μg each of the oligonucleotides indicated above (previously phosphorylated at the 5' position by a standard procedure) is reacted in a 100 ul volume containing 1 mM ATP, 10% polyethyleneglycol, and 100 units of T4 DNA ligase in the appropriate buffer at 13° C. for six hours. This step carries out the stochastic polymerization of the oligomers in the double stranded state and without cohesive ends. The resulting polymers are isolated by passage over a molecular sieve (Biogel P60) recovering those with 20 to 100 oligomers. After concentration, this fraction is again submitted to catalysis or polymerization by T4 DNA ligase under the conditions described above. Thereafter, as described above, those polymers which have assembled at least 100 oligomers are isolated.

c) Preparation of the Host Plasmid

The pUC8 expression vector is linearized by Sma1 enzyme in the appropriate buffer, as described above. The vector linearized by Sma1 does not have cohesive ends. Thus the linearized vector is treated by calf intestine alkaline phosphatase (CIP) at a level of one unit per microgram of vector in the appropriate buffer, at 37° C. for 30 minutes. The CIP enzyme is thereafter inactivated by two successive extractions with phenol-chloroform. The linearized and dephosphorylated vector is precipitated in ethanol, then redissolved in water at 1 mg/ml.

d) Ligation of Stochastic Genes to the Vector

Equimolar quantities of vector and polymers are mixed and incubated in the presence of 1000 units of T4 DNA ligase, 1 mM ATP, 10% polyethylene glycol, in the appropriate buffer, for 12 hours at 13° C. This step ligates the stochastic polymers in the expression vector and forms double stranded circular molecules which are, therefore, capable of transforming.

Transformation of Competent Clones.

Transformation of competent clones in carried out in the manner previously described.

III) Assembly of Stochastic Genes Starting from a Group of Heptamers

This procedure differs from that just discussed in that it utilizes palindromic heptamers which have variable cohesive ends, in place of stochastic sequences containing a smaller number of identical motifs.

a) Choice of a Group of Heptamers

It is possible, as an example, to use the following three palindromic heptamers:

5' XTCGCGA 3'

5' XCTGCAG 3'

5" RGGTACC 3' where X=A, G, C, or T and R=A or T, and where polymerization cannot generate any "stop" codons and forms triplets specifying all the amino acids. Clearly, it is possible to use other groups of heptamers fulfilling these same conditions.

b) Polymerization of a Group of Heptamers

This polymerization is carried out exactly in the fashion described above for octamers.

c) Elimination of Cohesive Extremities

The polymers thus obtained have one unpaired base on their two 5' extremities. Thus, it is necessary to add the complementary base to the corresponding 3' extremities. This is carried out as follows: 10 micrograms of the double stranded polymers are reacted with 10 units of the Klenow enzyme, in the presence of the four deoxynucleotidephosphates (200 mM) in a volume of 100 $\mu$l, at 4° C., for 60 minutes. The enzyme is inactivated by phenol chloroform extraction, and the polymers are cleansed of the residual free nucleotides by differential precipitation. The polymers are then ligated to the host plasmid (previously linearized and dephosphorylated) by following the procedures described above.

It is to be noted that the two last procedures which were described utilize palindromic octamers or heptamers which constitute specific sites of certain restriction enzymes. These sites are absent, for the most part, from the pUC8 expression vector. Thus, it is possible to augment considerably the complexity of an initial preparation of stochastic genes by proceeding in the following way: the plasmid DNA derived from the culture of $10^7$ independent transformants obtained by one of the two last procedures described above, is isolated. After this DNA is purified, it is partially digested by Cla1 restriction enzyme (procedure II) or by the Pst1 restriction enzyme (procedure III). After inactivation of the enzyme, partially digested DNA is treated with T4 DNA ligase, which has the effect of creating a very large number of new sequences, while conserving the fundamental properties of the initial sequences. This new ensemble of stochastic sequences can then be used to transform competent cells. In addition, the stochastic genes cloned by procedure II and III can be excised intact from the pUC8 expression vector by utilizing restriction sites belonging to the cloning vector and not represented in the stochastic DNA sequences.

Recombination within the stochastic genes generated by the two procedures just described, which result from the internal homology due to the recurrent molecular motifs, is an important additional method to achieve in vivo mutagenesis of the coding sequences. This results in an augmentation of the number of the new genes which can be examined.

Finally, for all the procedures to generate novel synthetic genes, it is possible to use a number of common techniques to modify genes in vivo or in vitro, such as a change of reading frame, inversion of sequences with respect to their promotor, point mutations, or utilization of host cells expressing one or several suppressor tRNAs.

In considering the above description, it is clear that it is possible to construct, in vitro, an extremely large number (for example, greater than a billion) different genes, by enzymatic polymerization of nucleotides or of oligonucleotides. This polymerization is carried out in a stochastic manner, as determined by the respective concentrations of the nucleotides or oligonucleotides present in the reaction mixture.

As indicated above, two methods can be utilized to clone such genes (or coding sequences): the polymerization can be carried out directly on a cloning expression vector, which was previously linearized; or it is possible to proceed sequentially to the polymerization then the ligation of the polymers to the expression vector.

In the two cases, the next step is transformation or transfection of competent bacterial cells (or cells in culture). This step constitutes cloning the stochastic genes in living cells where they are indefinitely propagated and expressed.

Clearly, in addition to the procedures which were described above, it is feasible to use all other methods which are appropriate for the synthesis of stochastic sequences. In particular, it is possible to carry out polymerization, by biochemical means, of single stranded oligomers of DNA or RNA obtained by chemical synthesis, then treat these segments of DNA or RNA by established procedures to generate double stranded DNA (cDNA) in order to clone such genes.

Screening or Selection of Clones of Transformed Host Cells

The further step of the procedure according to the invention consists in examining the transformed or transfected cells by selection or screening, in order to isolate one or several cells whose transforming or transfecting DNA leads to the synthesis of a transcription product (RNA) or translation product (protein) having desired property. These properties can be, for example, enzymatic, functional, or structural.

One of the most important aspects of the process, according to the invention, is that it permits the simultaneous screening or selection of an exploitable product (RNA or protein) and the gene which produces that product. In addition, the DNA synthesized and cloned as described, can be selected or screened in order to isolate sequences of DNA constituting products in themselves, having exploitable biochemical properties.

We shall now describe, as non-limiting examples, preferred procedures for screening and/or selection of clones of transformed cells such that the novel proteins are of interest from the point of view of industrial or medical applications.

One of these procedures rests in the idea of producing, or obtaining, polyclonal or monoclonal antibodies, by established techniques, directed against a protein or another type of molecule of biochemical or medical interest, where that molecule is, or has been rendered, immunogenic, and thereafter using these antibodies as probes to identify among the very large number of clones transformed by stochastic genes, those whose protein react with these antibodies. This reaction is a result of a structural homology which exists between the polypeptide synthesized by the stochastic gene and the initial molecule. It is possible in this way to isolate numbers of novel proteins which behave as epitopes or antigenic determinants on the initial molecule. Such novel proteins are liable to simulate, stimulate, modulate, or block the effect of the initial molecule. It will be clear that this means of selection or screening may itself have very many pharmacologic and biochemical applications. Below we describe, as a non-limiting example, this first mode of operation in a concrete case:

EGF (epidermal growth factor) is a small protein present in the blood, whose role is to stimulate the growth of epithelial cells. This effect is obtained by the interaction of EGF with a specific receptor situated in the membrane of epithelial cells. Antibodies directed against EGF are prepared by injecting animals with EGF coupled to KLH (keyhole limpet hemocyanin) to augment the immunogenicity of the EGF. The anti-EGF antibodies of the immunized animals are purified, for example, by passage over an affinity column, where the ligand is EGF or a synthetic peptide corresponding to a fragment of EGF. The purified anti-EGF antibodies are then used as probes to screen a large number of bacterial clones lysed by chloroform, and on a solid support. The anti-EGF antibodies bind those stochastic peptides or proteins whose epitopes resemble those of the initial antigen. The clones containing such peptides or proteins are shown by autoradiography after incubation of the solid support with radioactive protein A, or after incubation with a radioactive antibody.

These steps identify those clones, each of which contains one protein (and its gene) reacting with the screening antibody. It is feasible to screen among a very large number of colonies of bacterial cells or viral plaques (for example, on the order of 1,000,000) and it is feasible to detect extremely small quantities, on the order of 1 nanogram, of protein product. Thereafter, the identified clones are cultured and the proteins so detected are purified in conventional ways. These proteins are tested in vitro in cultures of epithelial cells to determine if they inhibit, simulate, or modulate the effects of EGF on these cultures. Among the proteins so obtained, some may be utilized for the chemotherapeutic treatment of epitheliomas. The activities of the proteins thus obtained can be improved by mutation of the DNA coding for the proteins, in ways analogous to those described above. A variant of this procedure consists in purifying these stochastic peptides, polypeptides, or proteins, which can be used as vaccines or more generally, to confer an immunity against a pathogenic agent or to exercise other effects on the immunological system, for example, to create a tolerance or diminish hypersensitivity with respect to a given antigen, in particular, due to binding of these peptides, polypeptides, or proteins with the antibodies directed against this antigen. It is clear that it is possible to use such peptides, polypeptides, or proteins in vitro as well as in vivo.

More precisely, in the ensemble of novel proteins which react with the antibodies against a given antigen X, each has at least one epitope in common with X, thus the ensemble has an ensemble of epitopes in common with X. This permits utilization of the ensemble or sub-ensemble as a vaccine to confer immunity against X. It is, for example, easy to purify one or several of the capsid proteins of the hepatitis B virus. These proteins can then be injected into an animal, for example, a rabbit, and the antibodies corresponding to the initial antigen can be recovered by affinity column purification. These antibodies may be used, as described above, to identify clones producing at least one protein having an epitope resembling at least one of the epitopes of the initial antigen. After purification, these proteins are used as antigens (either alone or in combination) with the aim of conferring protection against hepatitis B. The final production of the vaccine does not require further access to the initial pathogenic agent.

Note that, during the description of the procedures above, a number of means to achieve selection or screening have been described. All these procedures may require the purification of a particular protein from a transformed clone. These protein purifications can be carried out by established procedures and utilize, in particular, the techniques of gel chromatography, by ion exchange, and by affinity chromatography. In addition, the proteins generated by the stochastic genes can be cloned in the form of hybrid proteins having, for example, a sequence of the $\beta$-galactosidase enzyme which permits affinity chromatography against anti-$\beta$-galactosidase antibodies, and allows the subsequent cleavage of the hybrid part; that is to say, allowing separation of the novel part and the bacterial part of the hybrid protein. Below we describe the principles and procedures for selection of peptides or polypeptides and the corresponding genes, according to a second method of screening or selection based on the detection of the capacity of these peptides or polypeptides to catalyse a specific reaction.

As a concrete and non-limiting example, screening or selection in the particular case of proteins capable of catalyzing the cleavage of lactose, normally a function fulfilled by enzyme $\beta$-galactosidase ($\beta$-gal) will be described.

As above described, the first step of the process consists in generating a very large ensemble of expression vectors, each expressing a distinct novel protein. To be concrete, for example, one may choose the pUC8 expression vector with cloning of stochastic sequences of DNA in the Pst1 restriction site. The plasmids thus obtained are then introduced into a clone of $E.$ $coli$ from whose genome the natural gene for $\beta$-galactosidase, Z, and a second gene EBG, unrelated to the first but able to mutate towards $\beta$-gal function, have both been eliminated by known genetic methods. Such host cells ($Z^-$, $EBG^-$) are not able by themselves to catalyse lactose hydrolysis, and as a consequence, to use lactose as a carbon source for growth. This permits utilization of such host clones for screening or selection for $\beta$-gal function.

A convenient biological assay to analyze transformed $E.$ $coli$ clones for those which have novel genes expressing a $\beta$-gal function consists in the culture of bacteria transformed as described in petri dishes containing X-gal in the medium. In this case, all bacterial colonies expressing a $\beta$-gal function are visualized as blue colonies. By using such a biological assay, it is possible to detect even weak catalytic activity. The specific activity of characteristic enzymes ranges from 10 to 10,000 product molecules per second.

Supposing that a protein synthesized by a stochastic gene has a weak specific activity, on the order of one molecule per 100 seconds, it remains possible to detect such catalytic activity. In a petri dish containing X-gal in the medium, and the presence of the non-metabolizable inducer 1PTG (isopropyl-D-thiogalactoside) visualization of a blue region requires cleavage of about $10^{10}$ to $10^{11}$ molecules of X-gal per square millimeter. A bacterial colony expressing a weak enzyme and occupying a surface area of 1 mm² has about $10^7$ to $10^8$ cells. If each cell has only one copy of the weak enzyme, each cell would need to catalyse cleavage of between 10,000 and 100 of X-gal to be detected, which would require between 2.7 and 270 hours. Since under selective conditions it is possible to amplify the number of copies of each plasmid per cell from 5 to 20 copies per cell, or even to 100 or 1000, and because up to 10% of the protein of the cell can be specified by the new gene, the duration needed to detect a blue colony in the case of 100 enzyme molecules of weak activity per cell is on the order of 0.27 to 2.7 hours.

As a consequence of these facts, screening a very large number of independent bacterial colonies, each expressing a different novel gene, and using the capacity to express a β-gal function as the selection criterion, is fully feasible. It is possible to carry out screening of about 2000 colonies in one Petri dish of 10 cm diameter. Thus, about 20 million colonies can be screened on a sheet of X-gal agar of 1 square meter.

It is to be noted that bacterial colonies which appear blue on X-gal Petri dishes might be false positives due to a mutation in the bacterial genome which confers upon it the capacity to metabolize lactose, or for other reasons than those which result from a catalytic activity of the novel protein expressed by the cells of the colony. Such false positives can be directly eliminated by purifying the DNA of the expression vector from the positive colony, and retransforming Z⁻, EBG⁻ E. coli host cells. If the β-gal activity is due to the novel protein coded by the new gene in the expression vector, all those cells transformed by that vector will exhibit β-gal function. In contrast, if the initial blue colony is due to a mutation in the genome of the host cell, it is a rare event and independent of the transformation, thus the number of cells of the new clone of the transformed E. coli capable of expressing gal function will be small or zero.

The power of mass simultaneous purification of all the expression vectors from all the positive clones (blue) followed by retransformation of naive bacteria should be stressed. Suppose that the aim is to carry out a screening to select proteins having a catalytic function, and that the probability that a new peptide or polypeptide carries out this function at least weakly is $10^{-6}$, while the probability that a clone of the E. coli bacterial host undergoes a mutation rendering it capable of carrying out the same function is $10^{-5}$, then it can be calculated that among 20 million transformed bacteria which are screened, 20 positive clones will be attributable to the novel genes in expression vectors which each carries, while 200 positive clones will be the result of genomic mutation. Mass purification of the expression vectors from the total of 220 positive bacterial clones followed by retransformation of the naive bacteria with the mixture of these expression vectors will produce a large number of positive clones consisting of all those bacteria transformed with the 20 expression vectors which code for the novel proteins having the desired function, and a very small number of bacterial clones resulting from genomic mutations and containing the 200 expression vectors which are not of interest. A small number of cycles of purification of expression vectors from positive bacterial colonies, followed by such retransformation, allows the detection of very rare expression vectors truly positive for a desired catalytic activity, despite a high background rate of mutations in the host cells for the same function.

Following screening operations of this type, it is possible to purify the new protein by established techniques. The production of that protein in large quantity is made possible by the fact that identification of the useful protein occurs together with simultaneous identification of the gene coding for the same protein. Consequently, either the same expression vector can be used, or the novel gene can be transplanted into a more appropriated expression vector for its synthesis and isolation in large quantity.

It is feasible to apply this method of screening for any enzymatic function for which an appropriate biological assay exists. For such screenings, it is not necessary that the enzymatic function which is sought be useful to the host cell. It is possible to carry out screenings not only for an enzymatic function but for any other desired property for which it is possible to establish an appropriate biological assay. It is thus feasible to carry out, even in the simple case of β-gal function visualized on an X-gal Petri plate, a screening of on the order of 100 million, or even a billion novel genes for a catalytic activity or any other desired property.

Selection of Transformed Host Cells.

On the other hand, it is possible to use selection techniques for any property, catalytic or otherwise, where the presence or absence of the property can be rendered essential for the survival of the host cells containing the expression vectors which code for the novel genes, or also can be used to select for those viruses coding and expressing the desired novel gene. As a non-limiting, but concrete example, selection for β-galactosidase function shall be described. An appropriate clone of Z⁻ EBG⁻ E. coli is not able to grow on lactose as the sole carbon source. Thus, after carrying out the first step described above, it is possible to culture a very large number of host cells transformed by the expression vectors coding for the novel genes, under selective conditions, either by progressive diminution of other sources of carbon, or utilization of lactose alone from the start. During the course of such selection, in vivo mutagenesis by recombination, or by explicitly recovering the expression vectors and mutagenizing their novel genes in vitro by various mutagens, or by any other common technique, permits adaptive improvements in the capacity to fulfill the desired catalytic function. When both selection techniques and convenient bioassay techniques exist at the same time, as in the present case, it is possible to use selection techniques initially to enrich the representation of host bacteria expressing the β-gal function, then carry out a screening on a Petri plate on X-gal medium to establish efficiently which are the positive cells. In the absence of convenient bioassays, application of progressively stricter selection is the easiest route to purify one or a small number of distinct host cells whose expression vectors code for the proteins catalyzing the desired reaction.

It is possible to utilize these techniques to find novel proteins having a large variety of structural and functional characteristics beyond the capacity to catalyse a specific reaction. For example, it is possible to carry out a screen or select for novel proteins which bind to cis-regulatory sites on the DNA and thereby block the expression of one of the host cell's functions, or block transcription of the DNA, stimulate transcription, etc.

For example, in the case of E. coli, a clone mutant in the repressor of the lactose operon (i-) expresses β-gal function constitutively: due to the fact the lactose operator is not repressed. All cells of this type produce blue clones on Petri plates containing X-gal medium. It is possible to transform such host cells with expression vectors synthesizing novel proteins and carry out a screen on X-gal Petri plates in order to detect those clones which are not blue. Among those, some represent the case where the new protein binds to the lactose operator and represses the synthesis of β-gal. It is then feasible to mass isolate such plasmids, retransform, isolate those clones which do not produce β-gal, and thereafter carry out a detailed verification.

As mentioned above, the process can be utilized in order to create, then isolate, not only exploitable proteins, but also RNA and DNA as products in themselves, having exploitable properties. This results from the fact that, on one hand, the procedure consists in creating stochastic sequences of DNA which may interact directly with other cellular or biochemical constituents, and on the other hand, these sequences cloned in expression vectors are transcribed into RNA which are themselves capable of multiple biochemical interactions.

An example of the Use of the Procedure to Create and Select for a DNA which is Useful in Itself.

This example illustrates selection for a useful DNA, and the purification and study of the mechanism of action of regulatory proteins which bind to the DNA. Consider a preparation of the oestradiol receptor, a protein obtained by standard techniques. In the presence of oestradiol, a steroid sexual hormone, the receptor changes conformation and binds tightly to certain specific sequences in the genomic DNA, thus affecting the transcription of genes implicated in sexual differentiation and the control of fertility. By incubating a mixture containing oestradiol, its receptor, and a large number of different stochastic DNA sequences inserted in their vectors, followed by filtration of the mixture across a nitrocellulose membrane, one has a direct selection for those stochastic DNA sequences binding to the oestrodiol-receptor complex, where only those DNAs bound to a protein are retained by the membrane. After washing and elution, the DNA liberated from the membrane is utilized as such to transform bacteria. After culture of the transformed bacteria, the vectors which they contain are again purified and one or several cycles of incubation, filtration, and transformation are carried out as described above. These procedures allow the isolation of stochastic sequences of DNA having an elevated affinity for the oestradiol-receptor complex. Such sequences are open to numerous diagnostic and pharmacologic applications, in particular, for developing synthetic oestrogens for the control of fertility and treatment of sterility.

Creation and Selection of an RNA Useful in Itself

Let there be a large number of stochastic DNA sequences, produced as has been described and cloned in an expression vector. It follows that the RNA transcribed from these sequences in the transformed host cells can be useful products themselves. As a non-limiting example, it is possible to select a stochastic gene coding for a suppressor transfer RNA (tRNA) by the following procedure: a large number ($\geq 10^8$) of stochastic sequences are transformed into competent bacterial hosts carrying a "nonsense" mutation in the arg E. gene. These transformed bacteria are plated on minimal medium without arginine and with the selective antibiotic for that plasmid (ampicillin if the vector is pUC8). Only those transformed bacteria which have become capable of synthesizing arginine will be able to grow. This phenotype can result either from a back mutation of the host genome, or the presence in the cell of a suppressor. It is easy to test each transformed colony to determine if the arg+ phenotype is or is not due to the presence of the stochastic gene in its vector; it suffices to purify the plasmid from this colony and verify that it confers an arg+ phenotype on all arg E. cells transformed by it.

Selection of Proteins Capable of Catalyzing a Sequence of Reactions

Below we describe another means of selection, open to independent applications, based on the principle of simultaneous and parallel selection of a certain number of novel proteins capable of catalyzing a connected sequence of reactions.

The basic idea of this method is the following: given an initial ensemble of chemical compounds considered as building blocks or elements of construction from which it is hoped to synthesize one or several desired chemical compounds by means of a catalyzed sequence of chemical reactions, there exists a very large number of reaction routes which can be partially or completely substituted for one another, which are all thermodynamically possible, and which lead from the set of building blocks to the desired target compound(s). Efficient synthesis of a target compound is favored if each step of at least one reaction pathway leading from the building block compounds to the target compound is comprised of reactions each of which is catalyzed. On the other hand, it is relatively less important to determine which among the many independent or partially independent reaction pathways is catalyzed. In the previous description, we have shown how it is possible to obtain a very large number of host cells each of which expresses a distinct novel protein.

Each of these novel proteins is a candidate to catalyse one or another of the possible reactions, in the set of all the possible reactions leading from the ensemble of building blocks to the target compound. If a sufficiently large number of stochastic proteins is present in a reaction mixture containing the building block compounds, such that a sufficiently large number of the possible reactions are catalyzed, there is a high probability that one connected sequence of reactions leading from the set of building block compounds to the target compound will be catalyzed by a subset of the novel proteins. It is clear that this procedure can be extended to the catalysis not only of one, but of several target compounds simultaneously.

Based on this principle it is possible to proceed as follows in order to select in parallel a set of novel proteins catalyzing a desired sequence of chemical reactions:

1. Specify the desired set of compounds constituting the building blocks, utilizing preferentially a reasonably large number of distinct chemical species in order to increase the number of potential concurrent reactions leading to the desired target-compound.

2. Using an appropriate volume of reaction medium, add a very large number of novel stochastic proteins isolated from transformed or transfected cells synthesizing these proteins. Carry out an assay to determine if the target compound is formed. If it is, confirm that this formation requires the presence of the mixture of novel proteins. If so, then the mixture should contain a subset of proteins catalyzing one or several reaction pathways leading from the building block set to the target compound. Purify and divide the initial ensemble of clones which synthesize the set of novel stochastic proteins, the subset which is required to catalyse the sequence of reactions leading to the target compound.

More precisely, as a non-limiting example, below we describe selection of novel proteins capable of catalyzing the synthesis of a specific small peptide, in particular, a pentapeptide, starting from a building block set constituted of smaller peptides and amino acids. All peptides are constituted by a linear sequence of 20 different types of amino acids, oriented from the amino to the carboxy terminus. Any peptide can be formed in a single step by the terminal condensation of two smaller peptides (or of two amino acids), or by hydrolysis of a larger peptide. A peptide with M residues can thus be formed by M−1 condensation reactions. The number of reactions, R, by which a set of peptides having length 1, 2, 3, . . . M residues can be interconverted is larger than the number of possible molecular species, T. This can be expressed as $R/T \approx M-2$. Thus, starting from a given ensemble of peptides, a very large number of independent or partially independent reaction pathways leads to the synthesis of a specific target peptide. Choose a pentapeptide whose presence can be determined conveniently by some common assay technique for example HPLC (liquid phase high pressure chromatography), paper chromatography, etc. Formation of a peptide bond requires energy in a dilute aqueous medium, but if the peptides participating in the condensation reactions are adequately concentrated, formation of peptide bonds is thermodynamically favored over hydrolysis and occurs efficiently in the presence of an appropriate enzymatic catalyst, for example pepsin or trypsin, without requiring the presence of ATP or other high energy compounds. Such a reaction mixture of small peptides whose amino acids are marked radioactively to act as tracers with $^3H$, $^{14}C$, $^{35}S$, constituting the building block set can be used at sufficiently high concentrations to lead to condensation reactions.

For example, it is feasible to proceed as follows: 15 mg of each amino acid and small peptides having 2 to 4 amino acids, chosen to constitute the building block set, are dissolved in a volume of 0.25 ml to 1.0 ml of a 0.1M pH 7.6 phosphate buffer. A large number of novel proteins, generated and isolated as described above are purified from their bacterial or other host cells. The mixture of these novel proteins is dissolved to a final concentration on the order of 0.8 to 1.0 mg/ml in the same buffer. 0.25 ml to 0.5 ml of the protein mixture is added to the mixture of building blocks. This is incubated at 25° C. to 40° C. for 1 to 40 hours. Aliquots of 8 µl are removed at regular intervals, the first is used as a "blank" and taken before addition of the mixture of novel proteins. These aliquots are analyzed by chromatography using n-butanol-acetic acid-pyridine-water (930:6:20:24 by volume) as the solvent. The chromatogram is dried and analyzed by ninhydrin or autoradiography (with or without intensifying screens). Because the compound constituting the building block set are radioactively marked, the target compound will be radioactive and it will have specific activity high enough to permit detection at the level of 1–10 ng. In place of standard chromatographic analysis, it is possible to use HPLC (high pressure liquid chromatography) which is faster and simpler to carry out. More generally, all the usual analytic procedures can be employed. Consequently it is possible to detect a yield of the target compound of less than one part per million by weight compared to the compounds used as initial building blocks.

If the pentapeptide is formed in the conditions described above, but not when an extract is utilized which is derived from host cells transformed by an expression vector containing no stochastic genes, the formation of the pentapeptide is not the result of bacterial contaminants and thus requires the presence of a subset of the novel proteins in the reaction mixture.

The following step consists in the separation of the particular subset of cells which contain expression vectors with the novel proteins catalyzing the sequence of reactions leading to the target pentapeptide. As an example, if the number of reactions forming this sequence is 5, there are about 5 novel proteins which catalyse the necessary reactions. If the clone bank of bacteria containing the expression vectors which code for the novel genes has a number of distinct novel genes which is on the order of 1,000,000 all these expression vectors are isolated en masse and retransformed into 100 distinct sets of $10^8$ bacteria at a ratio of vectors to bacteria which is sufficiently low that, on average, the number of bacteria in each set which are transformed is about half the number of initial genes, i.e. about 500,000. Thus, the probability that any given one of the 100 sets of bacteria contains the entire set of 5 critical novel proteins is $(½)^5=\frac{1}{32}$. Among the 100 initial sets of bacteria, about 3 will contain the 5 critical transformants. In each of these sets, the total number of new genes is only 500,000 rather than 1,000,000. By successive repetitions, the total number of which is about 20 in the present case, this procedure isolates the 5 critical novel genes. Following this, mutagenesis and selection on this set of 5 stochastic genes allows improvement of the necessary catalytic functions. In a case where it is necessary to catalyse a sequence of 20 reactions and 20 genes coding novel proteins need to be isolated in parallel, it suffices to adjust the multiplicity of transformation such that each set of $10^8$ bacteria receives 80% of the $10^6$ stochastic genes, and to use 200 such sets of bacteria. The probability that all 20 novel proteins are found in one set is $0.8^{20}=0.015$. Thus, about 2 among the 200 sets will have the 20 novel genes which are needed to catalyse the formation of the target compound. The number of cycles required for isolation of the 20 novel genes is on the order of 30.

The principles and procedures described above generalize from the case of peptides to numerous areas of chemistry in which chemical reactions take place in aqueous medium, in temperature, pH, and concentration conditions which permit general enzymatic function. In each case it is necessary to make use of an assay method to detect the formation of the desired target compound(s). It is also necessary to choose a sufficiently large number of building block compounds to augment the number of reaction sequences which lead to the target compound.

The concrete example which was given for the synthesis of a target pentapeptide can also be generalized as follows:

The procedure as described, generates among other products, stochastic peptides and proteins. These peptides or proteins can act, catalytically or in other ways, on other compounds. They can equally constitute the substrates on which they act. Thus, it is possible to select (or screen) for the capacity of such stochastic peptides or proteins to interact among themselves and thereby modify the conformation, the structure or the function of some among them. Similarly, it is possible to select (or screen) for the capacity of these peptides and proteins to catalyse among themselves, hydrolysis, condensation, transpeptidation or other reactions modifying the peptides. For example, the hydrolysis of a given stochastic peptide but at least one member of the set of stochastic peptides and proteins can be followed and measured by radioactive marking of the given protein followed by an incubation with a mixture of the stochastic proteins in the presence of ions such as Mg, Ca, Zn, Fe and ATP or GTP. The appearance of radioactive fragments of the marked protein is then measured as described. The stochastic protein(s) which catalyse this reaction can again be isolated, along with the gene(s) producing them, by sequential diminution of the library of transformed clones, as described above.

An extension of the procedure consists in the selection of an ensemble of stochastic peptides and polypeptides capable of catalyzing a set of reactions leading from the initial building blocks (amino acids and small peptides) to some of the peptides or polypeptides of the set. It is therefore also possible to select an ensemble capable of catalyzing its own synthesis; such a reflexively autocatalytic set can be established in a chemostat where the products of the reactions are constantly diluted, but where the concentration of the building blocks is maintained constant. Alternatively, synthesis of such a set is aided by enclosing the complex set of peptides in liposomes by standard techniques. In a hypertonic aqueous environment surrounding such lipsomes, condensation reactions forming larger peptides lowers the osmotic pressure inside the lipsomes, drives water molecules produced by the condensation reactions out of the lipsomes, hence favoring synthesis of larger polymers. Existence of such an autocatalytic ensemble can be verified by two dimensional gel electrophoresis and by HPLC, showing the synthesis of a stable distribution of peptides and polypeptides. The appropriate reaction volume depends on the number of molecular species used, and the concentrations necessary to favor the formation of peptide bonds over their hydrolysis. The distribution of molecular species of an autocatalytic ensemble is free to vary or change due to the emergence of variant autocatalytic ensembles. The peptides and polypeptides which constitute an autocatalytic set may have certain elements in common with the large initial ensemble (constituted of coded peptides and polypeptides as given by our procedure) but can also contain peptides and polypeptides which are not coded by the ensemble of stochastic genes coding for the initial ensemble.

The set of stochastic genes whose products are necessary to establish such an autocatalytic set can be isolated as has been described, by sequential diminution of the library of transformed clones. In addition, an autocatalytic set can contain coded peptides initially coded by the stochastic genes and synthesized continuously in the autocatalytic set. To isolate this coded subset of peptides and proteins, the autocatalytic set can be used to obtain, through immunization in an animal, polyclonal sera recognizing a very large number of the constituents of the autocatalytic set.

These sera can be utilized to screen the library of stochastic genes to find those genes expressing proteins able to combine with the antibodies present in the sera.

This set of stochastic genes expresses a large number of coded stochastic proteins which persist in the autocatalytic set. The remainder of the coded constituents of such an autocatalytic set can be isolated by serial diminution of the library of stochastic genes, from which the subset detected by immunological methods has first been subtracted.

Such autocatalytic sets of peptides and proteins, obtained as noted, may find a number of practical applications.

We claim:

1. A process for the production of a peptide, polypeptide, or protein having a predetermined property, comprising the steps of:

producing stochastically generated polynucleotide sequences;

forming a library of expression vectors comprising said stochastically generated polynucleotide sequences;

culturing host cells comprising said library of expression vectors to produce said peptides, polypeptides, or proteins encoded by the stochastically generated polynucleotide. sequences;

screening or selecting said host cells, to thereby identify a host cell comprising an expression vector encoding a peptide, polypeptide, or protein having the predetermined property;

isolating a stochastically generated polynucleotide sequence from said expression vector which encodes the identified peptide, polypeptide, or protein;

using the isolated stochastically generated polynucleotide sequence to produce the peptide, polypeptide, or protein having the predetermined property.

2. A process for the production of a peptide, polypeptide, or protein having a predetermined property, comprising the steps of:

producing a population of stochastic polynucleotide sequences comprising stochastic synthetic polynucleotide sequences;

introducing the population of stochastic polynucleotide sequences thus obtained into host cells to produce transformed host cells;

cultivating the transformed host cells comprising said population of stochastic polynucleotide sequences to produce peptides, polypeptides, or proteins encoded by stochastic polynucleotide sequences;

screening or selecting a cell from said transformed host cells thereby identifying a cell producing the peptide, polypeptide, or protein having the predetermined property;

isolating the cell so identified, and growing the isolated cell under conditions to produce the peptide, polypeptide, or protein having the predetermined property.

3. A process for the production of a DNA having a selectable predetermined property, comprising the steps of:

producing DNA comprising stochastically generated polynucleotide sequences;

forming a library of expression vectors comprising said stochastically generated polynucleotide sequences;

culturing host cells comprising expression vectors from said library of expression vectors to express said DNA, and screening or selecting said host cells to identify a host cell comprising an expression vector expressing said DNA having the selectable predetermined property.

4. The process according to claim 3, wherein said selectable predetermined property comprises the capacity of said DNA to selectively bind to a compound.

5. A process for the production of a DNA having a selectable predetermined property, comprising the steps of:

producing a population of DNA comprising stochastic synthetic polynucleotide sequences;

introducing said population of DNA thus obtained into host cells to produce transformed host cells;

cultivating the transformed host cells;

screening or selecting the transformed host cells to identify a cell producing a DNA having said selectable predetermined property;

isolating the cell producing said DNA having said selectable predetermined property, and growing the isolated cell under conditions to produce the DNA having the selectable predetermined property.

6. A process for the production of a population of DNA comprising stochastic polynucleotide sequences, comprising the steps of:

linearizing an expression vector;

reacting said linearized expression vector with terminal transferase enzyme in the presence of predetermined ratios of deoxynucleotide-triphosphates of guanine, cytosine, thymidine, and adenine to form a stochastic polynucleotide sequence at each 3' extremity of said linearized vector;

hybridizing said stochastic polynucleotide sequence at a 3' extremity of said linearized vector, and synthesizing a second strand from said 3' ends of said hybridized vector.

7. A process for the production of a library of DNA molecules comprising stochastic sequences of polynucleotides, comprising the steps of:

producing stochastic sequences of polynucleotides;

ligating said stochastic sequences of polynucleotides into expression vectors;

transforming competent cells with said ligated expression vectors; and amplifying said transformed cells.

8. A process for the production of an RNA molecule having a selectable predetermined property, comprising the steps of:

producing a population of DNA molecules comprising stochastically generated polynucleotide sequences;

forming a library of expression vectors comprising said stochastically generated polynucleotide sequences;

culturing host cells comprising said expression vectors forming said library to express RNA from said DNA;

screening or selecting said host cells to identify a RNA having the selectable predetermined property.

9. A process for the production of an RNA molecule having a selectable predetermined property, comprising the steps of:

producing a population of DNA molecules comprising stochastic synthetic polynucleotide sequences, introducing said population of DNA molecules into host cells to produce transformed host cells;

cultivating said transformed host cells to produce a population of RNA comprising stochastic polynucleotide sequences;

screening or selecting said transformed host cells to identify a cell expressing an RNA molecule having the selectable predetermined property;

isolating the identified cell;

growing said isolated cell, and producing said RNA molecule having the selectable predetermined property.

10. The process according to claim 8 or 9, wherein said selectable predetermined property comprises the capacity of said RNA molecule to selectively bind a compound.

11. A process for the production of a library of RNA molecules comprising stochastic sequences of polynucleotide, comprising the steps of:

producing DNA comprising stochastic polynucleotide sequences;

ligating said DNA comprising stochastic polynucleotide sequences into expression vectors capable of expressing said DNA to produce said RNA;

transforming competent cells with said ligated expression vectors;

amplifying said transformed cells, and expressing said DNA to produce said library of molecule RNA.

12. A process for the production of a population of DNA comprising stochastic polynucleotide sequences, comprising the steps of:

linearizing an expression vector;

reacting said linearized expression vector with terminal transferase enzyme in the presence of stochastic ratios of deoxynucleotide-triphosphates of guanine, cytosine, thymidine, and adenine to form a stochastic polynucleotide sequence at each 3' extremity of said linearized vector;

hybridizing said stochastic polynucleotide sequence at a 3' extremity of said linearized vector; and synthesizing a second strand from said 3' ends of said hybridized vector.

* * * * *